US006443881B1

(12) United States Patent
Finger

(10) Patent No.: US 6,443,881 B1
(45) Date of Patent: Sep. 3, 2002

(54) OPHTHALMIC BRACHYTHERAPY DEVICE

(76) Inventor: Paul T. Finger, 1 Gracie Ter., Apt. 12A, New York, NY (US) 10028

( * ) Notice: Subject to any disclaimer, the term of this patent is extended or adjusted under 35 U.S.C. 154(b) by 20 days.

(21) Appl. No.: 09/589,868

(22) Filed: Jun. 6, 2000

(51) Int. Cl.$^7$ .............................................. A61N 5/00
(52) U.S. Cl. ............................................................. 600/1
(58) Field of Search ................................ 600/1, 2, 3, 4, 600/5, 6, 7, 8, 452, 459; 128/898

(56) References Cited

U.S. PATENT DOCUMENTS

| | | | | |
|---|---|---|---|---|
| 2,517,568 A | * | 8/1950 | Hissong | 600/7 |
| 4,850,377 A | * | 7/1989 | Parker et al. | 128/898 |
| 5,165,415 A | * | 11/1992 | Wallace et al. | 600/452 |
| 5,203,353 A | * | 4/1993 | Easley et al. | 128/898 |
| 5,637,073 A | * | 6/1997 | Freire | 600/3 |
| 6,102,844 A | * | 8/2000 | Ravins et al. | 600/8 |
| 6,183,410 B1 | * | 2/2001 | Jacobsen et al. | 600/3 |

OTHER PUBLICATIONS

Paul T. Finger, MD, Anthony Berson, MD, et al., "Ophthalmic Plaque Radiotherapy for Age–related Macular Degeneration Associated with Subretinal Neovascularization," *American Journal of Ophthalmology*, vol. 127, Feb. 1999, pp. 170–177.

Paul T. Finger, MD, Ray Iezzi, MD, et al., "Plaque–Mounted Diode–Light Transillumination for Localization Around Intraocular Tumors," *Archives of Ophthalmology*, vol. 117, Feb. 1999, pp. 179–183.

Paul T. Finger, MD, Ray Iezzi, MD, et al., "Diode–Light Transillumination for Ophthalmic Plaque Localization Around Juxtapapillary Choroidal Melanomas," *Int. J. Radiation Oncology Biol. Phys.*, vol. 44, No. 4, 1999, pp. 887–890.

Paul T. Finger, MD, "Radiation Therapy for Choroidal Melanoma," *Survey of Ophthalmology*, vol. 42, Nov.–Dec. 1997, pp. 215–232.

* cited by examiner

Primary Examiner—Eric F. Winakur
Assistant Examiner—David McCrosky

(57) ABSTRACT

A method and apparatus are provided for use in ocular brachytherapy. The device comprises a handle, an applicator coupled with said handle, and adapted to receive a source of radiation. The applicator is movable between a radiation shielding position and a position wherein radiation is allowed to reach the diseased area. A plurality of light-emitting diodes are located so as to define the area to be treated. A shield receives the applicator so as to shield the radiation source during insertion and positioning proximal the treatment site. An actuator moves the applicator between the shielded position and the treatment position. The method of treating macular degeneration employs the device according to the invention.

18 Claims, 1 Drawing Sheet

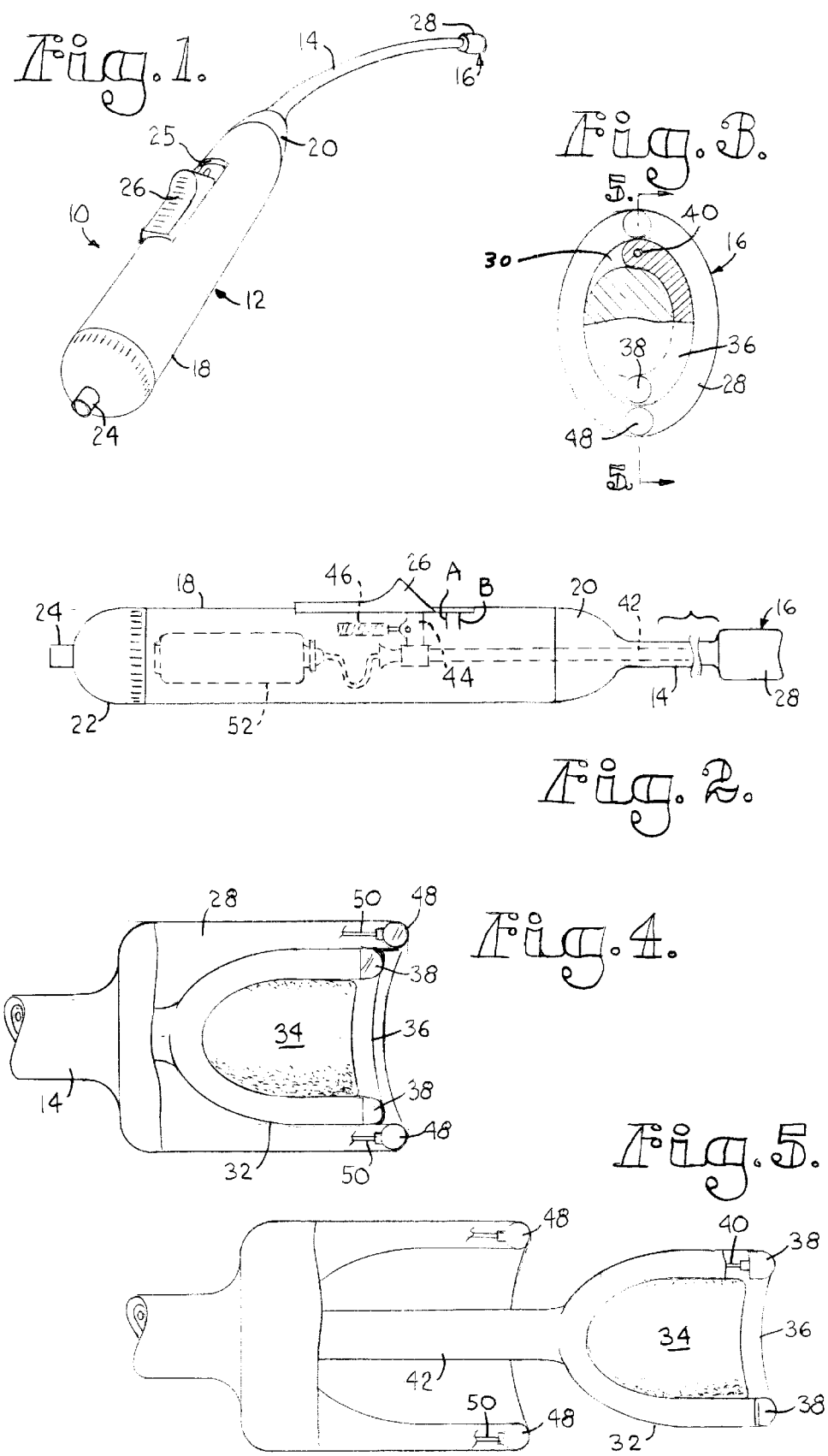

OPHTHALMIC BRACHYTHERAPY DEVICE

BACKGROUND OF THE INVENTION

The present invention relates generally to a device and method for the treatment of ocular diseases with radiation. Particularly, the device and method will be utilized to deliver a dose of radiation to a portion of the eye globe to treat subretinal neovascularization associated with age-related macular degeneration.

Macular degeneration is a pathologic process associated with subretinal neovascularization. The subretinal neovascularization allows fluid, blood, and lipids to leak beneath the surface of the retina. This leakage has detrimental effects on the health of the globe. For example, this leakage may cause hypoxia, retinal detachment or other eye condition problems. These conditions can cause scarring that will destroy the macular retina. The effect of the scarring on the macular retina can be severe. Specifically, it may cause irreversible loss of central vision.

There are currently two methods for treatment of macular degeneration. These methods utilize lasers to effect closure of subretinal neovascularization. While laser/photocoagulation is effective in closing subretinal neovascularization and preserving visual acuity, laser treatment is only effective in a small subset of patients, and can cause destruction of the overlying retina. The. other laser-assisted treatment utilizes light-activated dyes to close the subretinal neovascular vessels.

A new method utilized in the treatment of macular degeneration is radiation therapy. For example, low levels of ionizing radiation have been used to induce regression of choroidal hemangiomas, to stunt the growth of neovascular component of wounds, to close vascular malformations, and to treat subretinal neovascularization without destruction of the overlying retina. In one method of radiation treatment, the radiation is delivered to the affected area of the globe through the use of disk-like devices called ophthalmic plaques. Plaques are attached to the eye and remain there for a period of typically several days. However, the use of ophthalmic plaque radiation suffers from problems with the devices, localization beneath the macula, slow delivery requiring long treatment times, and fixed aperture sizes due to limitations on the ability to place relatively small objects in position beneath the macula (subretinal neovascularization) target. These side effects may be because these plaques are allowed to stay attached to the eye for a period of time, causing the irradiation of normal ocular tissue throughout the dose period.

Therefore, an improved device and method are needed for the treatment of intraocular neovascularization such as that associated with age-related macular degeneration to prevent scarring and to induce closure of normal blood vessels within the eye. The device of the invention may also have utility in ocular oncology applications.

BRIEF SUMMARY OF THE INVENTION

It is an object of the present invention to provide a device for nonpermanent variable exposures of ionizing radiation to specific places on the eye globe without excessive exposure of the normal ocular structures.

In accordance with the above object and other objects evident from the following description of a preferred embodiment of the invention, an ophthalmic brachytherapy device is provided for treating a diseased area with radiation. The device comprises a handle, an applicator coupled with said handle and adapted to receive a source of radiation with the applicator movable between a first radiation shielding position and a second position wherein radiation is allowed to reach the diseased area, a shield for receiving the applicator, a source of radiation coupled with the applicator, and an actuator for moving the applicator between first and second positions thus moving the radiation source between the two referenced positions (additional positions being optional). The invention also encompasses a method of treating macular degeneration which includes providing a source of radiation; placing the radiation source in an applicator which is movable between stored and treating positions; providing a shield to contain radiation while the applicator is being inserted and positioned; providing a light source proximal the radiation source, and moving the radiation source and the light source from the shielded position into a location proximal the eye globe.

By providing an ophthalmic brachytherapy device and method according to the present invention numerous advantages are realized. These include the provision of light sources both proximal and distal the radiation source for focusing light on the area to be treated. This facilitates precise placement of the radiation.

Another advantage of the present invention is that the radiation source is movable between treating and retracted positions. Shielding is provided in both positions, although to a greater degree in the retracted position thereby minimizing the exposure of normal tissue to the radiation source.

Still another of the advantages of the present invention is that by virtue of the radiation source being extendable and retractable the amount of radiation to which the diseased tissue is exposed may be controlled more precisely by controlling the extent to which the radiation source is extended from the shielding.

Still another advantage of the present invention is the presence of a light source which defines the area to be treated.

By providing an ophthalmic brachytherapy device in accordance with the present invention, numerous advantages are realized. For example, by providing nonpermanent variable exposure to the affected areas, normal ocular tissue will sustain less irradiation.

An additional advantage provided by the present invention is associated with the reduced amount of irradiation of the normal ocular structures during the positioning of the ophthalmic brachytherapy device.

DESCRIPTION OF THE DRAWING

In the accompanying drawings which form part of the specification and which are to be read in conjunction therewith, and in which like reference numerals are used to indicate like parts in the various views:

FIG. 1 is a perspective view of an ophthalmic brachytherapy device in accordance with the present invention;

FIG. 2 is a side elevational view, with portions cut away, of the brachytherapy device with other portions shown in broken lines;

FIG. 3 is a front elevational view of the applicator head of the device;

FIG. 4 is a side elevational view of the applicator head shown in FIG. 3, with portions broken away for purposes of illustration; and FIG. 5 is a side elevational view, similar to FIG. 4, with the applicator moved from its retracted to its extended position.

DETAILED DESCRIPTION OF THE INVENTION

Referring initially to FIG. 1, the brachytherapy device according to the present invention is designated generally by the numeral 10. Device 10 comprises a handle 12, a flexible stem 14, coupled with the handle, and an applicator head 16. Handle 12 comprises an elongated hollow body 18 which threadably receives a complemental nosepiece 20. An end cap 22 is threadably received on the end of body 18 opposite nosepiece 20. End cap 22 has an opening for receiving a switch 24. An elongated recess 25 in the outer wall of body 18 provides a track for an actuator lever 26.

Referring now to FIGS. 3–5, applicator head 16 includes a shield member 28 having a cavity 30 which receives the radiation applicator 32. Applicator 32 has a concave cross section and extends through an arc of approximately 180° to provide a receptacle for radiation source 34 (FIG. 3). Shield member 28 is of oval cross section and has an end which is concave so that it will generally conform to the eye globe. A source of radiation 34 is secured to the inside of applicator 32, such as by a suitable adhesive. A radiation shielding end plate 36 is of generally concave configuration with a radius of curvature which is approximately the same as the radius of curvature of the eye globe. This end plate precludes radiation from passing out the end of applicator head 16. The side walls of applicator 32 are also preferably formed from a material which offers some shielding for radiation source 34 so that radiation will be primarily directed out the open area opposite the applicator to the diseased tissue and limited from reaching healthy tissue, including the optic nerve.

In FIGS. 4 and 5 the front portion of shield member 28 has been broken away to reveal details of applicator 32. Two light-emitting diodes 38 are located in the side walls of applicator 32 and are coupled with an energy source via electrical leads 40. Applicator 32 is coupled with an actuator leg 42 which passes through stem 14, nosepiece 20 and body 18 before being coupled with a link 44 which is rigid with actuator lever 26. A coil spring 46 is coupled with link 44 so as to bias the link in the left-hand position shown in FIG. 2. Markings A and B on body 18 provide an indication of the degree to which applicator 32 has been extended.

Two more light-emitting diodes 48 are positioned in the end of shield 28 and are connected with an energy source by wire leads 50. Wire leads 40 and 50 are both connected with a battery 52 which is mounted inside of body 18. It is to be understood that other point light sources could be used in place of L.E.D.s 38 and 48. The strength and reflector size for the light sources is chosen so that, when applicator head 16 is in position, the lights will illuminate and define the area to be treated which will allow the physician to direct the radiation to the precise area where it is needed.

In use, the radiation source 34 is selected based upon the treatment to be effected. Both low energy and high energy radiation sources are contemplated. Once the radiation source 34 is in place within applicator 32, the applicator is inserted around the eye and maneuvered to the desired area of the globe. Lights 48 are activated by switch 24 to provide assistance for the physician who will be able to look inside the eye and see the area of treatment.

It is to be understood that shield 28 is formed from a radiation shielding material, well-known to those skilled in the art, so as to substantially preclude radiation from escaping the sides of the head as the applicator is moved into position. Once the applicator head is properly positioned with the face of applicator 32 against the optic nerve, actuator lever 26 is moved to extend applicator 32, as illustrated in FIG. 5 to a location adjacent the treatment site. Markings A and B provide the physician with a specific location for lever 26 corresponding to a desired position of applicator 32. Once the applicator 32 extends from shield 28, light-emitting diodes 38 are activated by switch 24 so as to define the area to be treated. The applicator 32 is also preferably provided with some shielding material so as to reduce radiation through the side walls and end wall 36, and instead concentrate the direction of the radiation outwardly through the open area opposite the application. It is to be understood, however, that complete shielding of radiation within applicator 32 may be neither possible nor desirable. Spring 46 biases applicator 32 into its fully retracted position, and thus when the treatment is completed, actuator lever is released so as to bring applicator 32 back within the confines of shield 28.

While the device of the present invention can be utilized in ocular oncology and other ophthalmic applications, it is particularly usefull as a brachytherapy device in treating the neovascular form of macular degeneration. While it is known that radiotherapy may be useful in treating macular degeneration associated with subretinal neovascularization, the present method comprises providing a source of radiation, placing the radiation source in an applicator which is movable from a stored position to a position proximal the eye globe. The method includes providing a shield to contain radiation while the applicator is being inserted and positioned and then moving the radiation source from the shielded position to the location proximal the eye globe. Preferably, the method encompasses providing a light source proximal the radiation source so that the two can be moved together from the shielded position into a location proximal the eye globe. A second light source distal the radiation source may also be provided. The method further encompasses removing the radiation source by retracting it into the shield. In the preferred form of the method of the invention, a first shield is provided which shields the radiation source during insertion and a second shield is provided which at least partially shields the radiation source after the latter has been moved proximal the eye globe while allowing radiation to reach the diseased area.

It is to be understood that radiation source 34 may be a radioactive element or a material such as plastic which has been impregnated with a radioactive material. In some cases, the radiation source may even be in a remote location and directed to applicator 32 via the opening in leg 42.

From the foregoing, it will be seen that this invention is one well-adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. An ophthalmic brachytherapy device for treating a diseased area with radiation, said device comprising:
   a handle,
   an applicator head comprising an applicator and a shield;
   said applicator coupled with said handle and adapted to receive a source of radiation, said applicator moveable between a first radiation shielded position and a second position wherein radiation is allowed to reach the diseased area;

said applicator comprising a stem and a receptacle, said receptacle located opposite said handle and containing said source of radiation;

the distal end of said applicator having a shape conforming to the shape of the eye globe;

said shield slidably receiving said applicator to contain radiation while said applicator is being inserted and positioned;

the distal end of said shield having a shape conforming to the shape of the eye globe;

an actuator coupled with said applicator and movable between first and second positions corresponding to said first and second positions of said applicator; and, a light source disposed at the terminal end of said applicator head which illuminates only a targeted radiation zone.

2. The invention of claim 1, further comprising said light source coupled with said applicator for directing a beam of light toward a diseased area.

3. The invention of claim 1, further comprising said light source coupled with said shield for directing a beam of light toward a diseased area.

4. The invention of claim 1, wherein said applicator has a concave terminal end for placement against the optic nerve.

5. The invention of claim 1, wherein said applicator comprises a receptacle for a radiation source, said receptacle comprising a radiation shielding material.

6. The invention of claim 1, wherein is included spring means coupled with said applicator for biasing said applicator toward said first position.

7. The invention of claim 1, wherein is included a battery for energizing said light source and a switch means for activating and deactivating said battery.

8. The invention of claim 1, further comprising said light source coupled with said applicator and said shield for directing a beam of light toward a diseased area.

9. An ophthalmic brachytherapy device for treating a diseased area of the eye globe with radiation, said device comprising:

a handle;

an applicator head comprising an applicator and a shield;

said applicator coupled with said handle and comprising a receptacle for receiving a radiation source, said applicator movable between a first radiation shielded position and a second position wherein radiation is allowed to reach the diseased area;

said applicator having a concave terminal end for placement against the optic nerve;

a light source coupled with said applicator head for directing a beam of light which illuminates only a targeted radiation zone;

said shield coupled with said handle for receiving said applicator and containing radiation while said applicator is being inserted and positioned; and an actuator coupled with said applicator, accessible from said handle and movable between first and second positions corresponding to said first and second positions of said applicator.

10. The invention of claim 9, wherein is included said light source coupled with said shield for directing a beam of light toward a diseased area.

11. The invention of claim 9, wherein is included said light source coupled with said applicator for directing a beam of light toward a diseased area.

12. The invention of claim 9, where is included said light source coupled with said applicator and said shield for directing a beam of light toward a diseased area.

13. A method of treating macular degeneration comprising:

providing a source of radiation;

placing said radiation source in an applicator which is movable from a stored position into a position proximal the eye globe;

providing a shield to contain radiation while said applicator is being inserted. and positioned;

providing a light source that illuminates only a targeted radiation zone; and moving said radiation source from its shielded position into a location proximal the treatment site.

14. The method of claim 13, wherein the moving step comprises moving said light source with said radiation source to illuminate only a targeted radiation zone.

15. The method of claim 14, wherein is included the step of utilizing said light source to define said treatment site.

16. The method of claim 14, further comprising removing said radiation source from the eye globe.

17. The method of claim 16, wherein said step of removing said radiation source comprises retracting said radiation source into said shield.

18. The method of claim 13, wherein said step of providing a shield to contain radiation includes providing a first shield which shields said radiation source during insertion and a second shield which partially shields said radiation source after the latter has been moved proximal the eye globe while allowing radiation to reach the diseased area.

* * * * *